(12) United States Patent
Sun (10) Patent No.: US 6,785,665 B2
(45) Date of Patent: Aug. 31, 2004

(54) METHOD AND EXPERT SYSTEM OF MOLECULAR MECHANICS FORCE FIELDS FOR COMPUTER SIMULATION OF MOLECULAR SYSTEMS

(75) Inventor: Huai Sun, 12561 Senda Panacea, San Diego, CA (US) 92129

(73) Assignee: Huai Sun, San Diego, CA (US)

( * ) Notice: Subject to any disclaimer, the term of this patent is extended or adjusted under 35 U.S.C. 154(b) by 309 days.

(21) Appl. No.: 10/139,806

(22) Filed: Apr. 16, 2002

(65) Prior Publication Data

US 2003/0195734 A1 Oct. 16, 2003

(51) Int. Cl.[7] .......................... G06F 17/00; G06F 15/00
(52) U.S. Cl. ............................ 706/60; 706/45; 702/183
(58) Field of Search ...................... 706/60, 45; 702/183

(56) References Cited

U.S. PATENT DOCUMENTS 5,715,371 A * 2/1998 Ahamed et al. ............... 706/10
6,625,569 B2 * 9/2003 James et al. ................. 702/183

* cited by examiner

*Primary Examiner*—George B. Davis (57) ABSTRACT

A method and system of generating molecular mechanics force fields for computer simulation of molecular systems, including a graphic user interface 101, extensible database 108 containing parameterized force fields, data and molecular models, interfaces to quantum mechanics 102 and molecular mechanics 107 calculations, and a computational engine 105. A force field attributes assigner 205 assigns force field type, functional forms and atom types. A parameter estimator 206 makes initial force field parameters based on the database and a set of mathematical formulas. A fit engine 207 fits complex potential energy surfaces efficiently.

15 Claims, 6 Drawing Sheets

METHOD AND EXPERT SYSTEM OF MOLECULAR MECHANICS FORCE FIELDS FOR COMPUTER SIMULATION OF MOLECULAR SYSTEMS

BACKGROUND OF THE INVENTION

The invention relates to the field of Computer Aided Molecular Design (CAMD) and, in particular, to systems and methods those simulate molecular behavior and predict the chemical and physical properties of molecules using computers (Molecular Modeling). Specifically, the invention relates to an expert system that automatically generates molecular mechanics force field parameters for computer simulation of molecular systems.

A molecular mechanics force field is a set of mathematical functions containing adjustable parameters. By adjusting the parameters, a molecular mechanics force field can be made to accurately describe inter-atomic interaction energies as functions of the atomic coordinates for a molecular system. Because all physical properties of a molecular system are determined by the interaction energies, a molecular mechanics force field is a fundamental component in molecular modeling.

Several general molecular mechanics force fields have been developed (e.g., CHARMM, AMBER, MM2, MM3, MMFF, CFF, COMPASS)[1–7]. These force fields perform well for molecular systems that have been explicitly parameterized, but not well for many others that have not been so parameterized because the required parameters are substituted by transferring parameters from similar molecules. Due to the massive number of possible chemical structures that can be made, it is impractical to have one force field that provides a complete coverage for all applications. Frequently, incomplete force field coverage is the stumbling block in "real-life" molecular modeling in various fields such as pharmaceutics, chemicals, and materials.

Generally speaking, two approaches, empirical and ab initio, have been taken to parameterize a force field. One can manually adjust the force field parameters to fit empirical data (for example, bond lengths, angles, conformational energies, vibrational frequencies, crystal structures, lattice energies, etc.) in a trial-and-error manner. Obviously, this approach is limited by the availability of the experimental data and is a very tedious and time-consuming process. Another approach is to derive the parameters from quantum mechanics ab initio data calculated for a group of model compounds. The ab initio approach can be used for any molecules prior to synthesizing the compounds so that it is ideal for applications in designing new molecules (for example, in the drug discovery process).

However, the ab initio parameterization still requires considerable efforts and experiences because the process entails more than simply the use of fitting procedures. It requires several steps consisting of selecting molecular models, preparing data, specifying force field models, setting initial parameters, fitting the data to the models, and validating the fit results. More importantly, the fit process itself is usually a difficult task due to the complexity of the problem. Hundreds of variables may be required in order to fit tens of thousands data points. Usually, simply applying a least-squares method to fit ab initio data leads to poor or unstable results. Empirical controls on the fit process have been extensively used in developing ab initio force fields, but so far, only a small number of experts in this field know how to do the work successfully. For most research scientists or engineers specializing in different fields, it is not a manageable task.

SUMMARY OF THE INVENTION

The present invention recognizes that high quality molecular mechanics force fields are required for successful computer modeling in chemical, pharmaceutical and material industries, and that it is currently a very difficult and time-consuming task to derive force field parameters. This invention remedies these problems by providing a method and a computer implemented expert system that can be used to make accurate force field parameters rapidly and easily from quantum mechanics ab initio data. Various technologies, as described in this specification and in the references identified in the enclosed LIST OF REFERENCES and cross-referenced throughout this document, have been utilized in constructing a novel process that make this system practical.

According to the invention, there is provided a method for developing molecular mechanics force field parameters for computer simulations of molecular systems automatically, comprising the steps of: creating or importing molecular models that represent said molecular systems; searching a database for matches between said molecular models and stored molecular models and retrieving stored parameters; preparing input data for quantum mechanics ab initio calculations; importing calculated data; selecting force field type and functional forms, assigning atom types; estimating initial force field parameters based on said database or a set of mathematical formulas; optimizing said initial force field parameters to fit the input data; validating the optimized force field parameters; and exporting the optimized force field parameters in required formats to external molecular mechanics simulation packages and saving the molecular models, input data and optimize force field parameters to the database.

The present invention provides a computer implemented expert system that implements said method. The system includes a database that contains developed force field parameters and the data utilized for the development, and a procedure that retrieves, stores, and searches said database. According to the invention, a knowledge base is established utilizing said database—future development becomes easier and faster with the amount of data accumulated increases. The system has a mechanism that allows selection of potential energy functional forms and adjustable parameters so that a custom-built force field type can be made to achieve the best performance and accuracy. This is especially useful for dealing with not-so-common molecular systems such as an interface between organic and inorganic molecules. The system provides a procedure that assigns force field attributes and generates default parameters automatically. Coupled with said database, estimated parameters can be made more accurately than those made using other methods. The system contains a robust procedure that utilizes several numerical algorithms and knowledge-based controls to fit very complicated energy surfaces efficiently. In addition, the system is supported by a platform-independent graphic user interface.

BRIEF DESCRIPTION OF THE DRAWINGS

A more complete appreciation of the present invention and many of the attendant advantages thereof will be readily obtained as the same becomes better understood by reference to the following detailed description when considered in connection with the accompanying drawings, wherein.

DETAILED DESCRIPTION OF THE PREFERRED EMBODIMENTS

In the preferred embodiment of the invention, a computer software program is implemented to enable fast development of molecular mechanics force field parameters.

Figure 1:
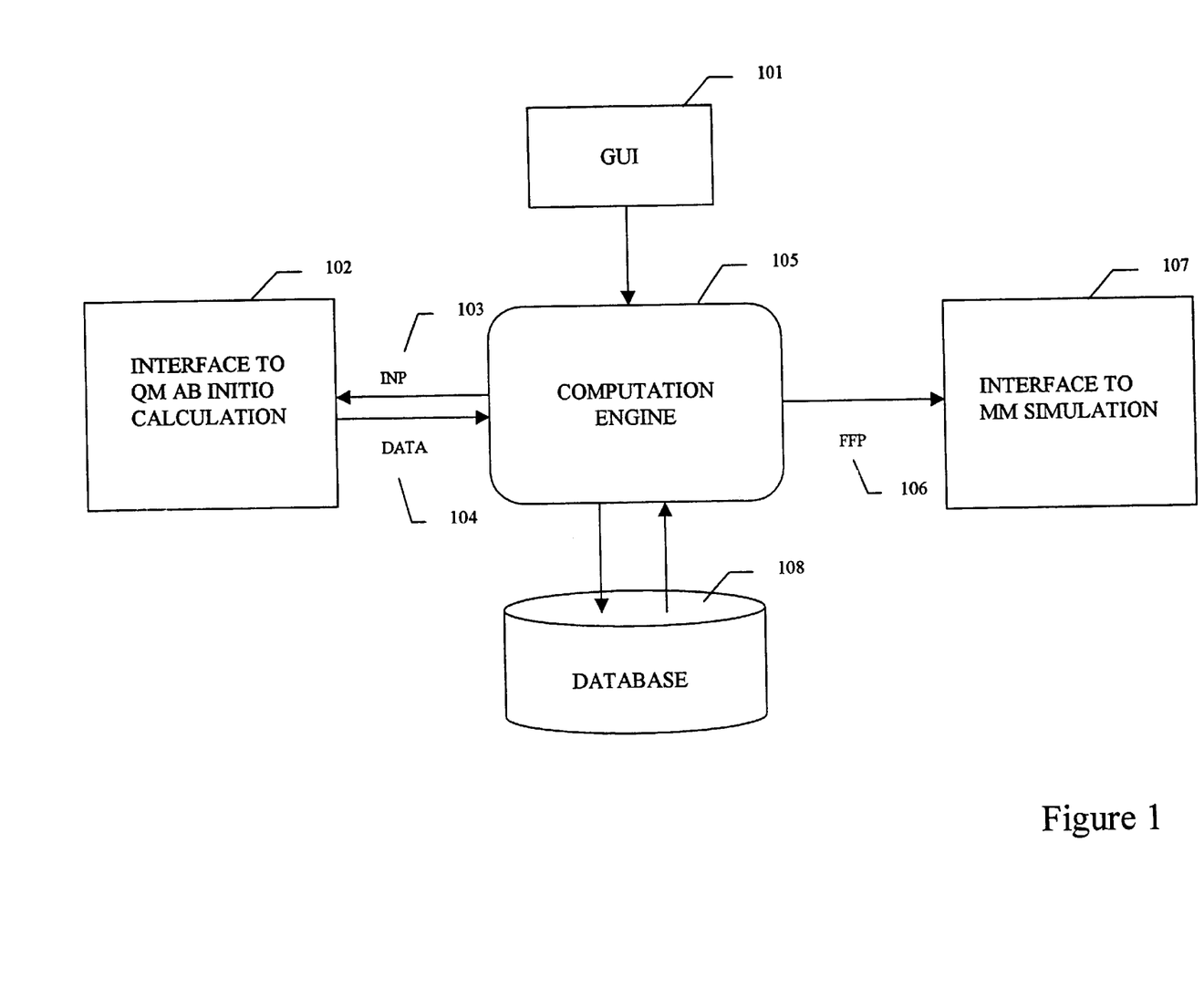
FIG. 1 is a top-level system block diagram and data flows for performing calculations, according to the present invention.

A high-level logical architecture of the program is illustrated in FIG. 1. The program consists of a graphical user interface (GUI) 101, a computational engine 105, a database 108, an interface 102 to quantum mechanics ab initio calculation software, and an interface 107 to a molecular mechanics simulation software.

Various computer languages can be used in implementing the software. For example, the graphic user interface 101 is implemented using JAVA, although any other language (for example, C, C++) may be used. The utilization of JAVA maximizes the platform independence that is, the program can be run without re-compiling the software on different operating systems such as Windows, Macintosh, Linux, Unix machines, etc. The computational engine 105 is implemented using C++ for maximum computational efficiency. The portability is enhanced by restricting language utilization to ANSI standard, enabling the program to be compiled on different platforms without modification of the source code.

The graphic user interface 101 includes several command modules; each provides a set of logically related functions. Users control the system through the graphic user interface 101. The database 108 provides an extensible knowledge base that supports the system; it initially contains force field parameters for common organics molecules and the data employed for deriving the parameters. The computational engine is the central part that connects all components together. It prepares input data 103 for the quantum mechanics calculations 102, reads the quantum mechanics calculation results data 104 and converts the data into force field parameters 106. The result force field parameters are delivered to molecular mechanics simulations 107. The computation engine uses the database 108 to retrieve or save force field parameters and related data.

The module 102 is an interface to external quantum mechanics ab initio software packages. The input data for these calculations include, for example, atom coordinates and calculation options (i.e. level of theory, basis sets, etc. [8]). The output data 104 of the ab initio calculation may include atom coordinates, molecular structural parameters e.g. bond lengths, angles, vibrational frequencies, conformational energies, atomic partial charges, total energies, gradients, and Hessian matrixes (first and second derivatives of the total energy with respect to the atom coordinates). Although it is commonly obtained from quantum mechanics ab initio calculations, the data 104 is not limited to quantum mechanics ab initio data. It also refers, for example, to any empirical or computational data, which can be obtained from experimental measurements or other types of calculations.

Furthermore, data input 104 is not mandatory. Without data, the expert system makes estimated parameters using the database 108 and/or an implemented default parameter generator, as described later in this specification with respect to FIG. 2c. If input data 104 is provided, the expert system then makes accurate parameters by fitting to the data.

The system is designed to support various force field types. A force field type refers to a specific combination of mathematical functional forms. A force field type plus corresponding parameters completely defines a force field. Several popular force field types e.g., CHARMM, AMBER, CFF, etc. [1–5] are supported. In addition, a library of common functions is prepared; by selecting various functional forms provided in the library, new force field types can be created.

Figure 2A:
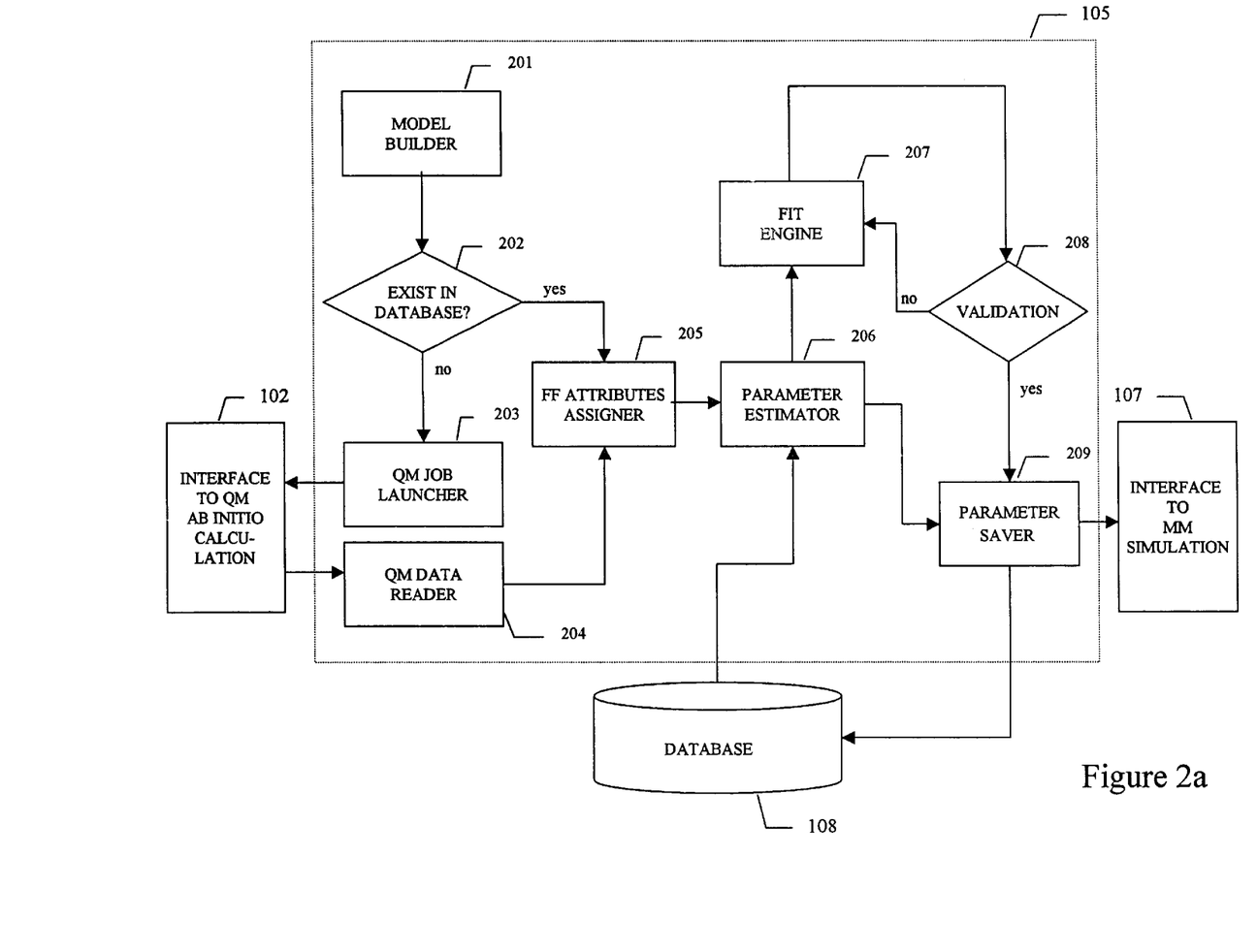
FIG. 2a is block diagram of data flows of the COMPUTATION ENGINE 105 component of FIG. 1, according to the present invention.

A sample operation of the computational engine 105 of FIG. 1 is shown in FIG. 2a. The operation of processes 205, 206 and 207 will be described in detail with respect to FIGS. 2b–2d, respectively.

The module 201 represents a builder that can be used to create a molecular model and a reader that reads in a molecular model, for example, from a disk file. The molecular model is a molecular system that can be a covalent-bonded molecule, a molecular cluster that contains several molecules, or a cluster of atoms. The molecular model is usually but not necessarily a smaller fragment of a large molecular system whose force field parameters need to be derived.

The model builder 201 utilizes mouse action techniques to enable sketching molecular structures on the screen. Any combination of the elements from the Periodic Table can be used for creating molecular models. The created models can be saved to disk files and retrieved later. Additional functions performed by module 201 include, for example, modifying model structures, viewing models in different styles, displaying model properties and attributes.

Module 202 searches the database 108 for a match of the input molecular model. Details on the operations of database 108 are given later in this Specification with respect to FIG. 3. If a match is found, there is no need to make new parameters for the input model, and modules 205, 206 and 209 are used to assign force field attributes, obtain the stored parameters, and export the model and parameters. If a match is not found, a new development is required.

Module 203 prepares quantum mechanics ab initio calculation jobs. Multiple conformations of a molecule or multiple configurations of a molecular or atomic cluster can be created in order to obtain a broad sample of the potential energy surfaces. These derived molecule models can be created by setting one or more internal coordinates of the initial model to different values. For example, to sample internal rotation energy profiles of an organic molecule, the derived models can be created by varying one or more dihedral angles of the internal rotations of the molecule; to sample inter-molecular interaction energy profiles of a molecular cluster, one may create several derived models by setting different atom-atom distances.

Computational options are also specified in the module 203 for quantum mechanics ab initio calculations. The options include, for example, level of theory e.g. HF, MP2, selection of the basis set 6–31G*, DZ, etc, [8] and where and how the calculations should be performed. The quantum mechanics calculation 102 may conducted by any commercial or academic software package, such as Gaussian98[9], GAMESS[10], etc.

The module 204 reads the data made by quantum mechanics calculations or other computational methods. This process also checks the input data for any errors or inconsistency.

The process module 205 assigns force field attributes for molecular models. It is further described in detail with respect to FIG. 2b.

Figure 2B:
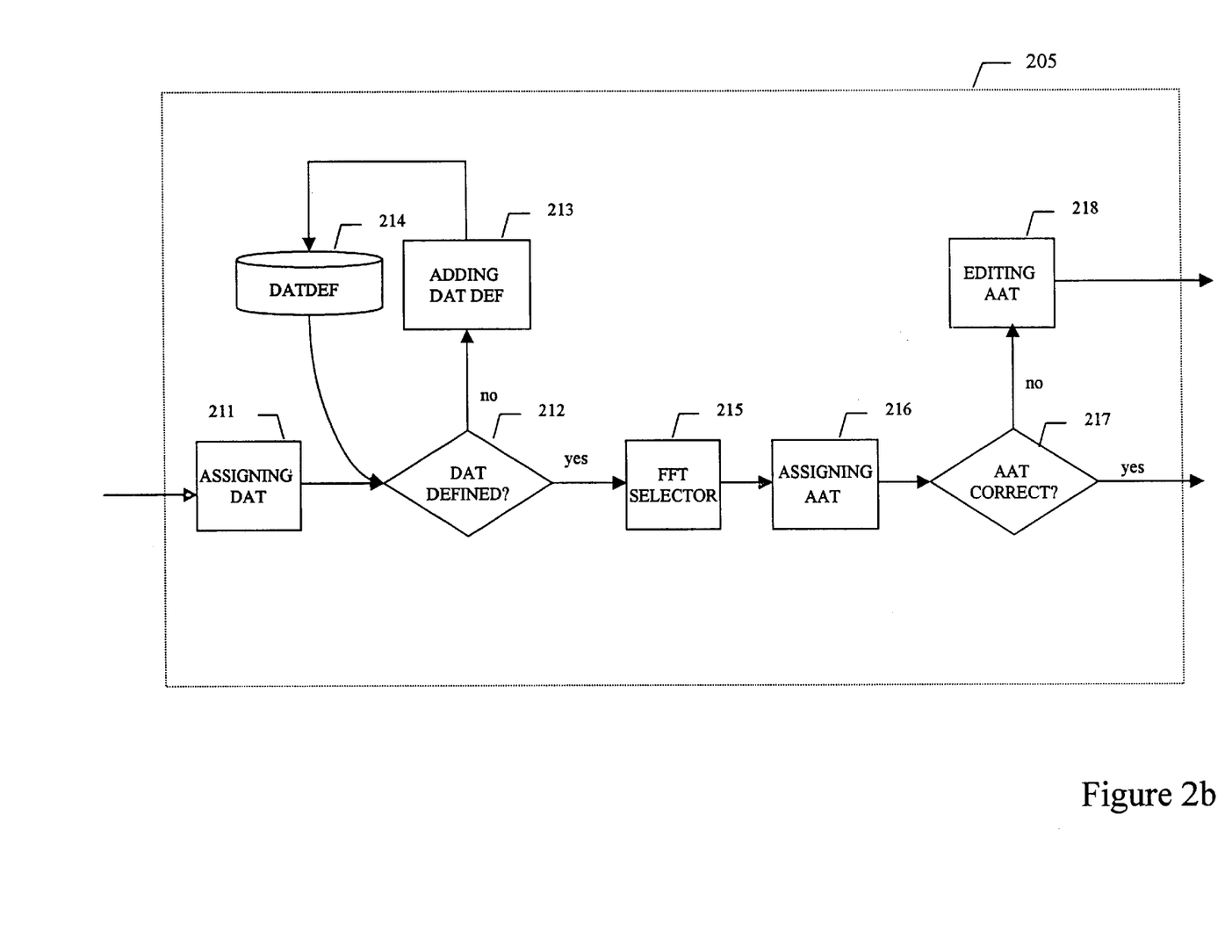
FIG. 2b is detailed flowcharts of the FF ATTRIBUTE ASSIGNER 205 component of FIG. 2a, according to the present invention.

Assigning force field attributes includes setting force field type and assigning atom types for molecular models.

Setting force field type means selecting functional forms that represent the force field interactions. Several packaged types—CFF, AMBER and CHARMM are provided the system. In addition, any functional forms provided in a library can be used. After the force field type is selected, the potential energy functions are fixed.

Two atom type systems are employed. Internally, each atom is assigned a Default Atom Type (DAT) regardless of what force field type is selected. This atom type system is used for generating initial parameters and managing fitting procedures. Another atom type system, Apparent Atom Type (AAT), is associated the force field type selected and used externally. When a result force field is exported to external simulation software, for example, the AAT system is exported with the parameters. This is mainly for consistency with external simulation software packages. For each atom in the molecular models, the DAT and AAT may or may not be the same.

The DAT system is assigned automatically when models are loaded, saved, modified or refined. The AAT system, however, is assigned through user interface, which can be done either automatically by using the assignment rules or manually by editing the AAT directly.

The DAT system is assigned based on a set of rules, which are listed as follows:
  Each DAT name includes 3–4 characters.
  The first two characters are the element symbol, if the symbol has only one character an underscore is used at the second place. (e.g., H_, C_, O_, Cl, Br).
  The third character is an integer (0–9) indicating coordination number (i.e., how many bonds are attached to this atom).
  The fourth character indicates special situations that the atom is in, for example:
  "c": in a small cyclic (3–4 member) molecule,
  "r": in resonance structure,
  "a": in an aromatic molecule,
  "p": in a highly polarized environment (e.g., high charge nearby),
  "+": Ion, and
  "−": Anion.

Each DAT has a set of basic atomic parameters that are used for generating estimated force field parameters. When these parameters are specified, the DAT is referred to as "defined". The parameters are:
  Atomic number
  DAT symbol
  Coordination number or number of bonds attached
  Preferred geometry: "NONE" "LINEAR" "BENT", "PLANAR", "PYRAMIDAL", "TETRAHEDRAL", "SQUARE", "BI-PYRAMIDAL", "SQUARE-PYRAMIDAL", "OCTAHEDRAL", "OTHER"
  Preferred valence bond radii
  Preferred bond angle where this atom is the center atom
  Van der Waals diameter
  Van der Waals energy
  Effective nuclei charge
  Torsion parameter More than two hundred (200) default atom types are defined in the system of the present invention; at least one DAT is defined for each element in the Periodic Table. Their basic atomic parameters are stored in the DATDEF database 214. Module 212 checks any assigned DAT for the molecular model, if the DAT does not have the basic parameters stored in the database DATDEF 214, a data input dialog 213 is provided for adding new parameters. The system provides a set of suggested parameters by retrieving similar entries in the database. The database DATDEF 214 can be retrieved, modified and saved at any time.

Module 215 specifies force field type. In addition to common force field types (CFF, CHARMM and AMBER), which are fixed combinations of functional forms, the system provides a function library so that user can create any combination of functional forms. For example, the following functions are provided in the library:

Bond
  b—bond length in Å.

$$f_b(b-b_o)^2 \tag{1-1}$$

$$f_{b2}(b-b_o)^2 + f_{b3}(b-b_o)^3 + f_{b4}(b-b_o)^4 \tag{1-2}$$

Angle
  θ—bond angle in radian.

$$K_\theta(\theta-\theta_o)^2 \tag{1-3}$$

$$K_{\theta 2}(\theta-\theta_o)^2 + K_{\theta 3}(\theta-\theta_o)^3 + K_{\theta 4}(\theta-\theta_o)^4 \tag{1-4}$$

Torsion
  φ—dihedral angle of bond torsion in radian.

$$K_\phi[1+\cos(n\phi-\phi_o)] \tag{1-5}$$

$$K_\phi[1-\cos(n\phi-\phi_o)] \tag{1-6}$$

$$K_{t1}(1-\cos\phi)+K_{t2}(1-\cos 2\phi)+K_{t3}(1-\cos 3\phi) \tag{1-7}$$

Improper Torsion
  χ—dihedral angle of improper torsion in radian.

$$K_\chi(\chi-\chi_o)^2 \tag{1-8}$$

$$K_\chi[1+\cos(n\chi-\chi_o)] \tag{1-9}$$

$$K_\chi[1-\cos(n\chi-\chi_o)] \tag{1-10}$$

Out-of-plane Angle
  χ—out-of-plane angle in radian.

$$K_\chi(\chi-\chi_o)^2 \tag{1-11}$$

$$K_\chi[1+\cos(n\chi-\chi_o)] \tag{1-12}$$

$$K_\chi[1-\cos(n\chi-\chi_o)] \tag{1-13}$$

Nonbonded Interaction
  R—atom-atom distance in Å.

$$\varepsilon\left[\left(\frac{m}{n-m}\right)\left(\frac{R}{R^o}\right)^{-n} - \left(\frac{n}{n-m}\right)\left(\frac{R}{R^o}\right)^{-m}\right] \tag{1-14}$$

$$\varepsilon\left[\left(\frac{1}{1-6/\alpha}\right)\left(\frac{6}{\alpha}e^{\alpha(1-R/R^o)} - \left(\frac{R}{R^o}\right)^{-6}\right)\right] \tag{1-15}$$

The Apparent Atom Type (AAT) definition is also based on an atom's topological connectivity and attributes. However, the patterns that define all atom types are stored in user-editable files.

A pattern-matching process is implemented in the system of present invention to match each atom with the stored patterns to assign atom types in an automatic assignment mode. Each definition of pattern consists of a substructure specification and associated atom attributes. The substructure specification is defined by a bond type (single, double, partial double, or triple) and an element symbol. The atom attributes include coordination numbers, aromaticity, hybridization, ring size, elements allowed and disallowed, etc. For example, the following strings define an AAT named "HR1":

Define HR1
H[—C[—N[—H]][=N]]
atom 2: coord=3, aromatic=yes, ringsize=5
atom 3: ringsize=5
End When executing an automatic assignment, the system searches and compares the definitions of atom types and returns the best matched atom type for each atom in the opened models. The matches are numerically measured using two matching scores. The first, matching level, equals the number of atoms matched in the defined substructure. A match means that not only the bond type and element symbol are the same, but also all attributes specified are satisfied. Another score, match points, is the total number of attributes matched. The second score is useful when two or more definitions yield the same match level; match points can be used to break the tie.

AAT definitions are relevant to force field type selected. A set of typing rules are created according to literature and saved in text files. These files can be modified to change default definitions.

Since different atom type symbols may be used in different simulation packages, the automatically assigned AAT may need to be modified. Module 217 is used to check if the automatically assigned AAT symbols need to be modified. The editing is processed in module 218.

Figure 2C:
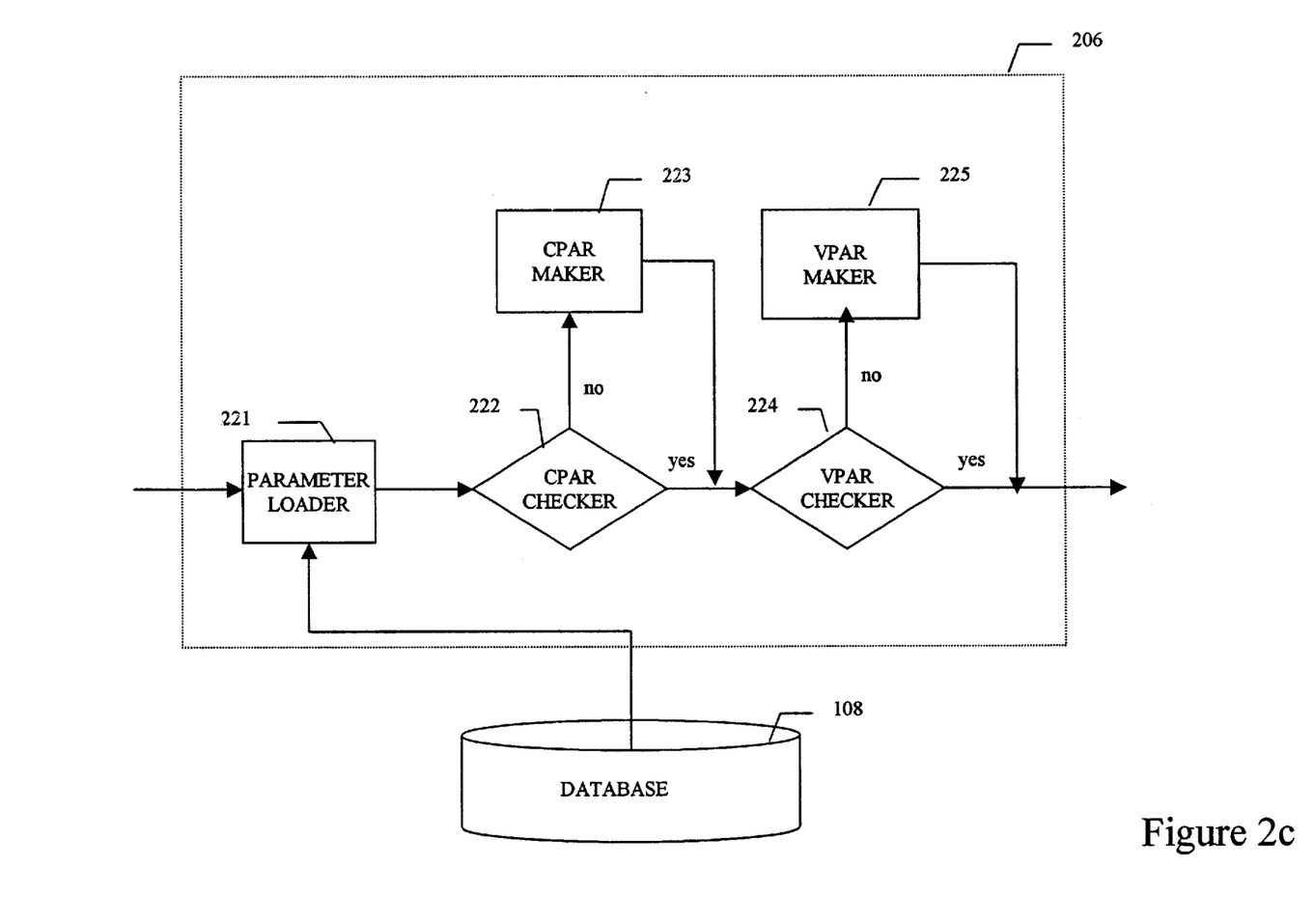
FIG. 2c is detailed flowcharts of the PARAMETER ESTIMATOR 206 component of FIG. 2a, according to the present invention.

FIG. 2C illustrates in detail the module 206 for initializing parameters. The parameter initializer loads parameters from the database 108, checks the coverage of parameters and makes new initial parameters if necessary, and exists with all required parameters as output.

Process 221 performs the task of loading parameters from the database 108. It is used in two ways. If the input molecule model exists in the database 108 and the required parameters have been parameterized for the selected force field type, the corresponding parameters are retrieved. If the molecule model is not in the database, or the required parameters have not been parameterized, estimated values of the required parameters are calculated by averaging values of same interaction terms in different molecule models found in the database 108. Details are explained later in the specification with respect to FIG. 3.

After loading parameters from the database, series modules from 222 to 225 are utilized to check if all required parameters are provided. Process 222 checks the charge parameters. If the model of molecule has been parameterized and retrieved successfully, all charge parameters are present. Otherwise, new charge parameters must be created.

The new charge parameters are made in module 223. The charge parameters are derived from atomic partial charges. Atomic charges are charge distributions based on atoms, which can be calculated using quantum mechanics methods (e.g. Mulliken or ESP methods)[7, 8], the charge equilibrium method [11], or any other charge assignment methods. The charge parameters are parameters used by force field programs to assign atomic charges.

In order to make charge parameters, atomic partial charges must be assigned first. The atomic partial charges can be taken from quantum mechanics calculations (the ESP charges or Mulliken Charges) or be calculated using the charge equilibrium method. A charge equilibrium method similar to the published charge equilibrium method [11] is implemented. The basic parameters used to calculate the charge distribution are the ionization potentials (IP) and the electron affinities (EA) of atoms, which are collected from the literature and included in a data file.

Three types of charge parameters, atom, atom-type and bond-type based, can be used. The atom based charge parameters are uniquely assigned based on atoms; each atom in the molecule may have different charge values. The atom-type based parameters are defined on atom types; each atom type has a charge parameter and all atoms that have the same atom type share one parameter. The bond-type based parameter is also called a bond charge increment [1], which is characterized by atom types of two bonded atoms. Suppose atom i and j are bonded and their corresponding atom types are at(i) and at(j), the bond-type based charge parameter $\delta_{at(i),at(j)}$ represents a charge relocation from atom j to atom i. For example, $\delta_{at(i),at(j)}=0.5$ means atom i receives 0.5 of an electron and atom j receives -0.5 of an electron. For any atom i, the net charge is a sum of all relevant bond charge increments, as follows:

$$q_i = \sum_j \delta_{at(i),at(j)} \qquad (2\text{-}1)$$

In the above discussion, the definition of bond-type charge parameter automatically leads to a neutral total charge for any chemically bonded system. In order to describe charged systems, the bond-type based charge parameters must be supplemented by atom or atom-type based charge parameters.

The charge parameters are derived from the atomic partial charges by minimizing the squares of deviations. For example, supposing a set of atomic partial charges are given for a molecule of M atoms, the partial charge vector is denoted by:

$$Q=\{q_1, q_2, q_3, \ldots q_M\} \qquad (2\text{-}2)$$

and the charge parameters can be calculated by solving the following equation:

$$AP=Q \qquad (2\text{-}3)$$

where P is the charge parameter vector given by:

$$P=\{p_1, p_2, p_3, \ldots p_N\} \qquad (2\text{-}4)$$

and A is an assignment matrix:

$$A=(a_{ij})_{M \times N} \qquad (2\text{-}5)$$

The assignment matrix is defined in the following way:
If $P_j$ is atom based, A is a unit matrix, the charge parameters are equivalent to atomic partial charges.
If $P_j$ is atom-type based:

$a_{ij}=1$, if $p_j=q_{at(i)}$;

$a_{ij}=0$, otherwise.

If, however, $P_j$ is bond-type based, then:

$a_{ij}=1$ if $p_j=\delta_{at(i),at(k)}$;

$a_{ij}=-1$ if $p_j=\delta_{at(k),at(i)}$;

$a_{ij}=0$ otherwise.

In the above equations, M (number of atoms) is usually greater than N (number of the charge parameters), so that that equation AP=Q does not have an exact solution in general. A singular value decomposition (SVD) method [12] is used to solve this equation. By solving the equation using the SVD method, the obtained P has smallest values that yield closest solutions in a sense of least squares.

If valence parameters are missing, step 225 is used to generate default valence parameters. The default parameters are calculated based on default atom types (DAT). The following energy terms are calculated:

Bond Stretch

For a bond connect two atoms i and j, two parameters, reference bond length and force constant, are calculated:

$$r_{ij}^o = r_i^* + r_j^* \quad (2\text{-}6)$$

$$f_b = 700 \frac{Z_i^* Z_j^*}{(r_{ij}^o)^3}$$

where $r_i^*$ and $r_j^*$ are the DAT bond radii, and $Z_i^*$ and $Z_j^*$ are the DAT effective charges.

Bond Angle

Three parameters, reference equilibrium angle, force constant and multiplicity in range of $[0, \pi])$ are calculated for a bond angle consisting atoms (i-j-k). The force constant is given as follows:

$$f_a = 700 \frac{Z_i Z_k}{(r_{ik}^0)^3} \quad (2\text{-}7)$$

where $r_{ik}^{o2} = r_{ij}^{o2} + r_{jk}^{o2} - 2r_{ij}^o r_{jk}^o \cos\theta_j^o$.

The multiplicity n in $[0, \pi]$ and the reference equilibrium angle depend on the DAT preferred geometry of the central atom j, as shown in the following table:

| Preferred Geometry | N | $\theta_j^0$ |
|---|---|---|
| SQUARE (SQ) | 2 | 90, 180 |
| SQPYRAMIDAL | 2 | 90, 180 |
| BIPYRAMIDAL: | 6 | 90, 120, 180 |
| OCTAHEDRAL: | 2 | 90, 180 |
| OTHERS | 1 | $\theta_j^*$ |

In the above table $\theta_j^*$ is the preferred DAT bond Angle of the atom j.

Torsion

Dihedral angle formed by four consecutively bonded atoms (i-j-k-l) are represented by three parameters, reference torsion angle, energy barrier height and multiplicity in range of $[0, 2\pi]$.

The torsion energy barrier height is defined by:

$$f_t = \sqrt{\tau_j^* \tau_k^*} / N_T \quad (2\text{-}8)$$

where $\tau_j^*$, $\tau_k^*$ are DAT torsion barrier parameters for atom j and k and $N_T$ is the total number of torsion angles about bond (j-k). The multiplicity n and reference torsion angle are determined by preferred geometries of center atoms j and k, as shown in the following table:

| J | K | n | $\phi_0$ |
|---|---|---|---|
| TETRAHEDRAL | TETRAHEDRAL | 3 | 180.0 |
| TETRAHEDRAL | PYRAMIDAL | 6 | 0.0 |
| TETRAHEDRAL | PLANAR | 6 | 0.0 |
| TETRAHEDRAL | BENT | 3 | 180.0 |
| PYRAMIDAL | PYRAMIDAL | 6 | 180.0 |
| PYRAMIDAL | PLANAR | 6 | 180.0 |
| PYRAMIDAL | BENT | 6 | 180.0 |
| PLANAR | PLANAR | 2 | 0.0 |
| PLANAR | BENT | 6 | 0.0 |
| BENT | BENT | 3 | 180.0 |

Out-of-plane Distortion

The out-of-plane distortion for a tri-bonds center consists of four atoms (denoted as i-j-k-l, where j is the central atom) is measured by an out-of-plane angle between the bond (i-j) and the plane of (j-k-l). In most cases, this term is not used. Two parameters are defined when the preferred geometry of atom j is PYRAMIDAL or PLANAR. In this case, the reference angle is set to 0.0 and the force constant typically is 0.0 and 5.0 respectively.

VDW Energy

The van der Waals interactions are calculated using two parameters, VDW well depth and diameters, as specified in terms of the Lennard-Joules 12–6 function:

$$E_{VDW} = \varepsilon_i \left[ \left( \frac{d_i^*}{r} \right)^{12} - 2\left( \frac{d_i^*}{r} \right)^6 \right] \quad (2\text{-}9)$$

where $\varepsilon_i = \varepsilon_i^*$ $d_i = d_i^* \quad (2\text{-}10)$

In the above equations, $\varepsilon_i^*$ and $d_i^*$ are DAT VDW parameters.

The calculated values are converted into force field parameters of functions specified for the selected force field type. The conversion is straightforward because all of the calculated values have clear correspondence in the parameters of the functions used.

The database 108 plays an important role in the system. It not only stores parameterized models so that no previous work would be repeated but also provides a novel method of using transferred parameters.

Currently, force fields are distributed as data files. Each force field file contains lines of interaction terms specified by atom types and parameters. For example, the following is a typical line of entry for a bond interaction term:

| CA CB | 450.0 | 1.424 | Model A |
|---|---|---|---|
| CA CB | 460.0 | 1.404 | Model B |
| CA CB | 461.0 | 1.405 | Model C |

The interaction term contains two atom types: CA, CB, and two parameters: the force constant and reference bond length. Note that only the atom types specify an interaction. This has a profound consequence. Since these parameters are derived based on one or a few model compounds. When the force field is used for a new molecule, if it happens that the same pair of atom types is used for a bond in the molecule, the same parameters will be used—a process which is generally referred as transferring parameters [7]. Since the difference between the new molecule and original molecules is not clear (in most cases, the information about the original model compounds is not immediately available), large errors can be introduced into the calculation without any indication.

Using the database approach, not only the parameters but also the information about the original model compounds are directly available. For example, the same interaction term may be found in several compounds. The following entries may be found for the same bond term as above example in the database:

| CA | CB | 460.0 | 1.404 |
|---|---|---|---|

In addition, the system provides a set of statistic analysis tools for analyzing the data. By comparing the parameters and the model compounds associated with them, the user can see how transferable the parameters are, identify the best approximation among the available parameters of the molecule, and estimate the uncertainty of using the transferred parameters.

Therefore, the system has a self-learning mechanism in its utilization of the database. The more data the database contains, the more choices the user may have, and the more accurate the approximated parameters can be.

Figure 3:
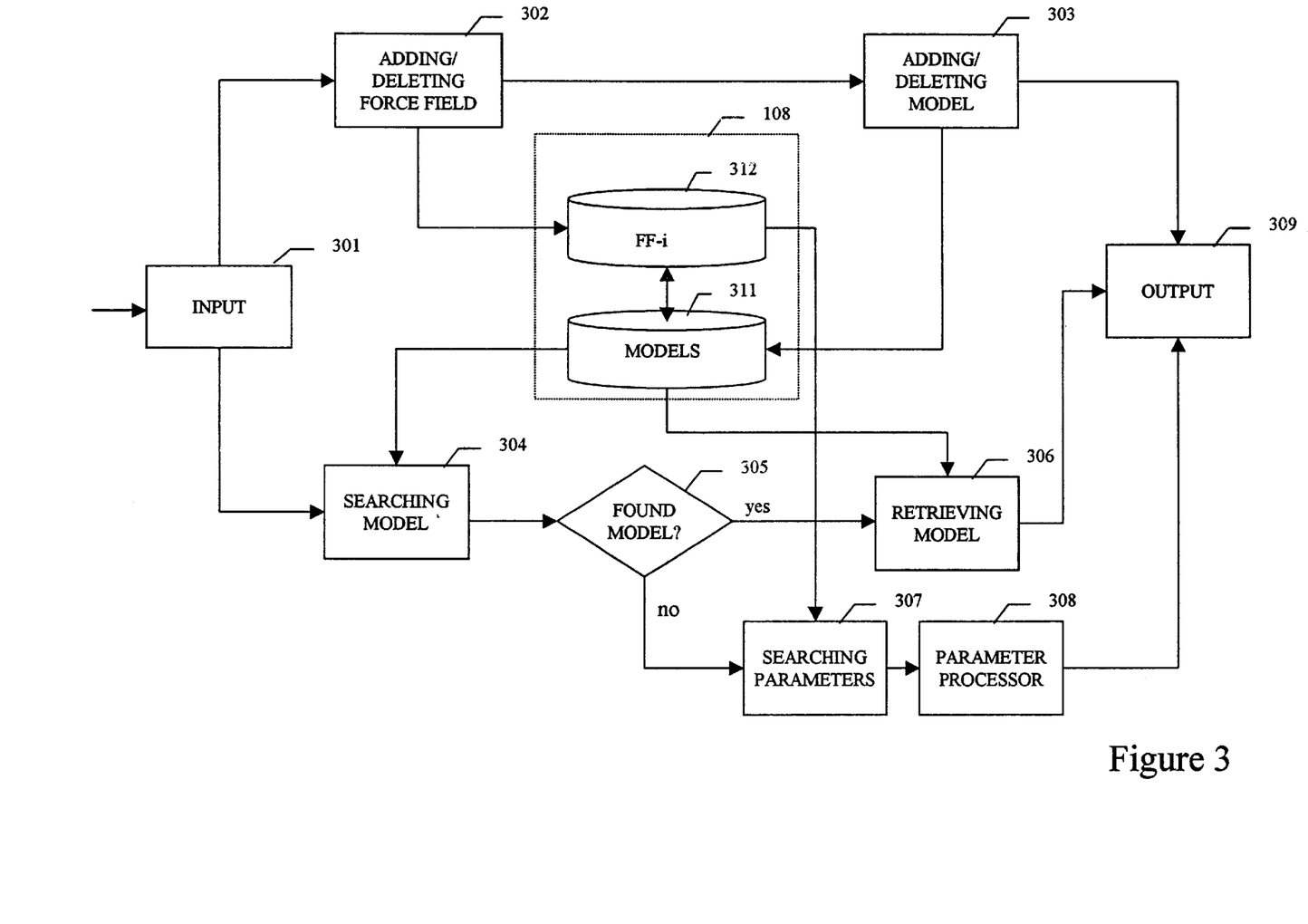
FIG. 3 is block diagram of data flows for managing the DATABASE module 108 of FIG. 1, according to the present invention.

One implementation of the database, for example, is illustrated in FIG. 3. The database 108 is subsequently divided into model database 311 and force field database 312. There may be several databases. Each contains logically related contents (i.e. divided by force field types including user created force field types). The separation of the model database from the force field databases enables quick access of either the models or force field parameters, which are two main usages of the database in this preferred embodiment.

To further enhance the performance of accessing the database, each of the databases is divided into two components: an index table and a content table. The index table contains identifiers or key words and the indices to the positions where the corresponding contents are stored in the content table. The indices are small, sorted files that can be loaded into computer RAM memory for quick access. The content tables are potentially large, randomly accessible disk files.

The index table of the model database contains, for example, the following members:
Molecule name
Chemical formula
Structure pattern string
Index to the content table
The content table of the model database contains, for example:
Molecule name
Chemical formula
Structure pattern string
Molecular properties (weight, CAS Registry Number, etc.)
Physical properties (density, etc.)
Cartesian coordinates and connectivity table
Force field (1)
Force field (2)
. . .
Force field (N)
Data (1)
Data (2)
. . .
Data (M)
In the above model content table, multiple force fields and data lists are allowed.

The force field entry contains the following elements:
Force field attributes—atom types and charges
Index to the force field table
The data entry contains:
Level of theory
Cartesian coordinates
Atomic charges
Energies
Energy derivatives
The index table of the force field database contains:
Function identifier (e.g. "BOND", "TORSION", etc . . . )
Interaction term identifier (string of DAT symbols)
Level of theory (e.g. HF/6-31G*, MP2/DZ2PF)
Index to the content table
The main content table of the force field database contains:
Function identifier (e.g. "BOND", "TORSION", etc . . . )
Interaction term identifier (string of DAT symbols)
Level of theory (e.g. HF/6-31G*, MP2/DZ2PF)
ADT symbols
Parameter array The operation of the database 108 can be described as follows. Specifically, INPUT 301 accepts commands and/or data, translates the commands into search queries, and sends the queries and/or data to appropriate operation modules.

If the request is for the addition or deletion of a model and its content data, module 302 is utilized to add or delete the force field entries first. After the force field database is updated, the model database, which contains indices to the force field database, is modified using module 303. To add or delete an entry in the database, the content table is modified first by adding new ensues or by removing target entries. Then the index table is updated.

If the request is to load a model or estimate force field parameters for a model, module 304 is used to search the model first. The search query may be a molecule name, a chemical formula, or a structural string which can be used for a pattern match. The search is conducted on the index table only. Only a complete match will be returned. Module 305 checks if the target model exists in the database. Several matches may be returned. The indices of the matching entries are collected and passed to module 306, which presents the matching items in the GUI 101 to allow the user to select the one to be used and then retrieves the data.

If no match of the queried model is found, module 307 is used to search similar parameters for the input model. The search queries contain the function identifier and the interaction term identifier, and may be limited to a particular level of theory specified through GUI 101. The input query uses default atom types (DAT) that identifies an energy term in the force field. The reason default atom types (DAT) are used instead of apparent atom types (AAT) is because the DAT is static and independent of the force field type used. Multiple entries may be found from the database for each interaction term.

The module 308 processes the result parameters and prepares a force field parameter table for the input model. If only one entry is found for the required interaction term, the parameters are entered into the parameter table in their original values. If multiple entries are found for the required interaction term, mean values and standard deviations are calculated for the parameters and the results are added in the parameter table.

As shown in FIG. 2a, the parameters obtained from step 206 can be directly exported using step 209 to internal or external molecular mechanics calculations 107. This process would be undertaken if the model of molecule created in step 201 has been parameterized and successfully retrieved from the database 108, or if the user simply wished to use the initialized parameters, which in many cases, are the best approximations using the transferability of force field parameters. If the program is used to derive new force field parameters, next step 207 is taken and the details are explained as follows.

Figure 2D:
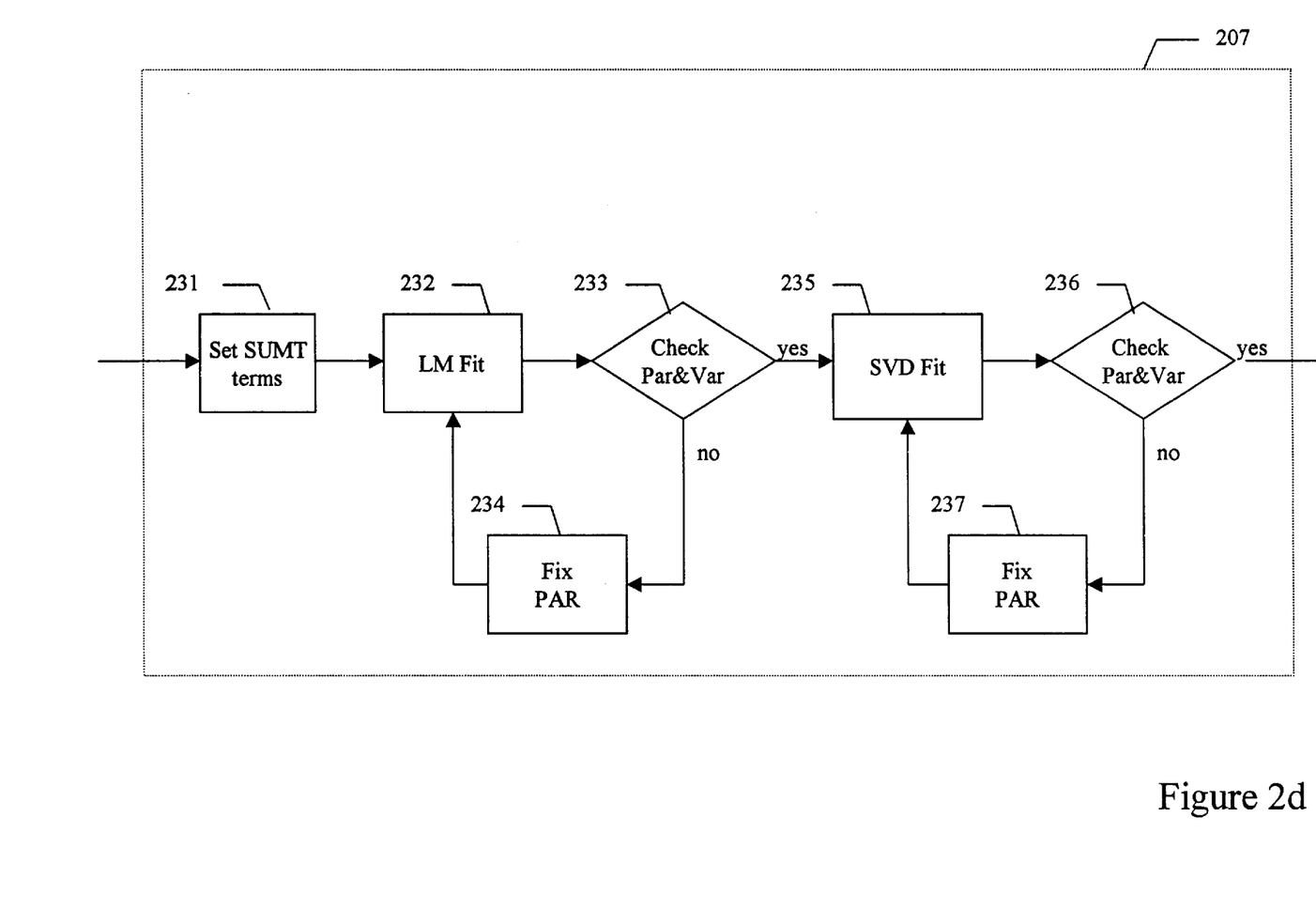
FIG. 2d is detailed flowcharts of the FIT ENGIEN 207 component of FIG. 2a, according to the present invention.

The fit process step 207 is further described with respect to FIG. 2d. Three components are taken as input: the initial parameters, the baseline data, and the molecular models. Upon exiting this step, the parameters are optimized to fit the input baseline data.

To construct a molecular mechanics force field from ab initio data is frequently a difficult task. The challenge arises from several factors associated with the least squares fit: ambiguous combinations of parameters that are defined based on redundant internal coordinates, inadequate functional forms employed to represent the energy surfaces, and incomplete samples of data points on the surfaces. Generally speaking, the fit is both over-determined (more data points than variable parameters) and under-determined (ambiguous combination of correlated parameters), and the ambiguities are often unknown prior to the fit process.

It has been found in this invention that the difficulties stated above can be largely reduced or eliminated by utilizing several numerical algorithms and by controlling the fitting procedures and adjustable parameters during the fit procedure.

The LM/SUMT fitting module 232 uses a Levenberg-Marquardt non-linear least squares fit method [12, 13] plus sequentially unconstrained minimization techniques (SUMT) [14] to perform initial fitting of the parameters. Using the SUMT method, the least squares problem is written as a conditional minimization:

$$\chi^2 = \sum_{i=1}^{N} \left[ \frac{y_i - y(x_i; \{a_k : k = 1, M\})}{\sigma_i} \right]^2 + \sum_{k}^{S} P_k (a_k - a_k^o)^2 \quad (3\text{-}1)$$

where the first term is the normal least squares expression of the input data $y_i$ and the calculated data is $y(x_i;\{a_k:k=1,M\})$. The second term is the penalty term in which some of the parameters are restrained to a set of preferred values:

$$a_k \approx a_k^o$$

and the penalty factor $P_k$ is an adjustable factor which controls how hard the restriction is. Note that by setting all penalty factors to zeros, the above equation is reduced to normal least squares equation.

The module 231 analyzes the baseline data and set the penalty function terms. The preferred values are set based on the analysis of the input data. For example, the reference values $a_k^o$ for bond lengths and angles are taken from the optimized values in the input data of the quantum mechanics optimized structures.

Upon finishing the initial fit, parameters obtained are screened in step 233 for any excessively large values. If any errors are detected, the corresponding parameters are fixed to initial values, which are best approximations in most cases, and the fit process 232 is repeated.

The SVD fitting step continues the fit procedure. By limiting the variables to linear terms only, the least squares problem is reduced to solving a linear equation [12]:

$$\chi^2 = \sum_{i=1}^{N} \left[ \frac{y_i - \sum_{k=1}^{M} a_k X_k(x_i)}{\sigma_i} \right]^2 = |A \cdot a - B| \quad (3\text{-}2)$$

If the parameters to be fit are redundant—some parameters are linear combinations of others, matrix A is singular or numerically very close to singular. The SVD method can be used to find the solution.

The SVD method is based on a theorem that A can be written as a product of three matrixes (decomposition):

$$A = UWV^T \quad (3\text{-}3)$$

where $$W = [\text{diag}(1/w_i)] \quad (3\text{-}4)$$

and the solution to the equation 3-2 is given by:

$$a = \sum_{i=1}^{M} \left( \frac{U_{(i)} \cdot b}{w_i} \right) V_{(i)} \quad (3\text{-}5)$$

If the matrix A is singular or close to singular, some of elements $(1/w_i)$ of the W matrix are very large quantities. The advantage of using the singular value decomposition (SVD) method [12] is that by setting the very large elements $(1/w_i)$ to zeros, the redundancy problem can be significantly reduced. In practice, a threshold is specified; when the value of $w_i$ is less than the threshold, the $(1/w_i)$ term is set to zero in the W matrix. In the present invention, a small value of the threshold is given initially. When the fit is done, the obtained parameters and their variances are screened. If any parameters or their variances are excessively large, the threshold value is increased by a factor of ten and the fit is repeated. This procedure automatically produces the best solution to equation 3-2 for the given variables.

Referring back to FIG. 2a, after the fit, a validation process step 208 is taken. The models of molecule are optimized using the obtained force field parameters and the results are compared with the input data. The results include optimized internal coordinates, vibrational frequencies, conformational energies, etc. The comparisons between the calculated and input data are analyzed statistically and displayed on to the GUI 101.

If the validation step 208 fails to pass, the fit procedure can be repeated by varying fitting options or by adding more constraints on the parameters. If the fit is satisfactory by the standard of the validation results, the exporter module 209 is used to save the results. It exports the results to disk files in formats adopted for user-selected external molecular mechanics simulation packages. The module 209 also saves the results (e.g., force field parameters, models of molecule) and data files to the database 108.

LIST OF REFERENCES

[1] Maple J. R.; Hwang, M. J.; Stockfisch, T. P.; Dinur U; Waldman, M.; Ewig, C. S.; Hagler, A. T., *J. Comput. Chem.*, 1994, 15, 162.

[2] Mackerell A. D.; Wiorkiewiczkuczera, J.; Karplus, M., *J. Amer. Chem. Soc.*, 1995, 117, 11946.

[3] Cornell, W. D.; Cieplak, P.; Bayly, C. I.; Gould, I. R.; Merz, K. M; Ferguson, D. M.; Spellmeyer, D. C.; Fox, T.; Caldwell, J. W.; Kolman, P. A., *J. Amer. Chem. Soc.*, 1995, 117, 5179.

[4] Allinger, N. L.; Chen K. S.; Katzenellenbogen J. A.; Wilson, S. R.; Anstead, G. M., *J. Comput. Chem.*, 1996, 17, 747.

[5] Halgren, T. A., *J. Comput. Chem.*, 1996, 17, 490.

[6] Sun, H. *J. Phys. Chem. B. Vol.*, 1998, 102, 7338.

[7] *Reviews in Computational Chemistry*, K. B. Lipkowitz and D. B. Boyd, Editors, Wiley, New York. Vol. I-II (1990-1991).

[8] *Ab Initio Molecular Orbital Theory*; Hehre, W. J.; Radom, L.; Schleyer, P. v. R.; and Pople, J. A. John Wiley & Sons, New York, 1986.

[9] Gaussian98 is a quantum mechanics software package distributed by Gaussian Inc., USA.

[10] Gamess is a quantum mechanics software package distributed by Dr. Mark Gordon at Iowa State University, USA.

[11] Dasgupta, S; Goddard, W. A, J. Chem. Phys. 1989, 90, 7207.

[12] Press, W. H., Flannery, B. P., Teukolsky, S. A & Vettering, W. T., Numerical recipes in C. The Art of Scientific Computing, 2nd edn, Cambridge University Press. 1992

[13] Marquardt, D. W. J. Soc. Ind. Appl. Math., 1963, 11, 431.

[14] Dennis, J. E., Schnabel, R. B., Numerical Methods for Unconstrained Optimization and Nonlinear Equations, 1996.

What is claimed is:

1. A method for developing molecular mechanics force field parameters for computer simulations of molecular systems, which include molecules, clusters of molecules and clusters of atoms, comprising of the following steps:
    a) creating or importing molecular models that represent said molecular systems to be parameterized;
    b) searching a database for matches between said molecular models and stored molecular models and retrieving stored parameters if complete matches are found;
    c) preparing input data for quantum mechanics ab initio calculations for said molecular models;
    d) importing calculated data of said quantum mechanics ab initio calculations for said molecular models;
    e) selecting force field type and functional forms, and assigning atom types to said molecular models;
    f) estimating initial force field parameters for said molecular models based on said database or a set of mathematical formulas for said molecular models;
    g) optimizing said initial force field parameters to fit said input data of quantum mechanics ab initio calculations;
    h) validating the optimized force field parameters; and
    i) exporting said optimized force field parameters in required formats to external molecular mechanics simulation packages and saving the molecular models, input data and optimize force field parameters to said database.

2. The method of claim 1, wherein said database is a database of molecular models, their force field parameters and the data for deriving the force field parameters, and the searching step b) comprises:
    performing a primary match of molecular names, formulas, or structures of said molecular models against the same properties of molecular models stored in said database;
    performing a secondary match of force field type and computational level of theory of said molecular models against the same properties of molecular models stored in said database, discovered in said primary match; and
    retrieving force field parameters of the molecular models stored in said database, discovered in said secondary match.

3. The method of claim 1, wherein said force field type is a collection of mathematical functions that describe interaction energies and said atom types are symbols representing atoms in different chemical environments, the selecting force field step e) comprises:
    selecting said force field type from a function library;
    assigning default atom types to said molecular models; and
    assigning apparent atom types to said molecular models.

4. The method of claim 3, wherein said default atom types are symbols used independent of force field types and the step of assigning default atom type comprises:
    assigning default atom types based on chemical structures and atomic attributes of said molecular models;
    searching a database of default atom types for a match against stored default atom types and retrieving basic atomic parameters of default atom types discovered; and
    adding basic atomic parameters if the default atom type is not stored in the database.

5. The method of claim 1, whereon said initial force field parameters are parameters made based on the said database or said mathematical formulas, and the estimating step f) comprises the steps of:
    creating a list of required force field parameters for said molecular models based on said force field type and said atom types;
    searching the required force field parameters from said database and calculating said initial force field parameters based on parameters discovered; and
    calculating remaining required force field parameters using default mathematical formulas.

6. The method of claim 5, wherein the searching step comprises:
    performing a primary match of functional form and computational level of theory of said required force field parameters against the same properties of force field parameters stored in said database;
    performing a secondary match of atom types associated with said required force field parameters against the same properties of force field parameters stored in said database, discovered in said primary match; and
    retrieving force field parameters discovered in said secondary match.

7. The method of claim 1, wherein the optimizing step comprises:
    optimizing the said initial force field parameters to fit said input data based on Levenberg-Marquardt non-linear least squares fit method and sequentially unconstrained minimization technique (SUMT) method;
    optimizing the linear terms of said initial force field parameters to fit said input data based on singular value decomposition (SVD) method; and
    analyzing result force field parameters, fixing parameters with excessive values or variances discovered in the analysis, and repeating the optimization process.

8. The method of claim 7, wherein the step of using sequentially unconstrained minimization technique (SUMT) method comprises:
    identifying reference values based on said input data of optimized structures of quantum mechanics ab initio calculations; and adding penalty terms into the least squares minimization.

9. The method of claim 7, wherein the step of optimizing the linear terms comprises:

setting the filter factor to a minimal value initially;

optimizing the linear terms of said initial force field parameters to fit said input data based on singular value decomposition (SVD) method; and adjusting the filter factor automatically depending on the said analyzing results in claim 5 and repeating the optimization procedure.

10. The method of claim 7, wherein the step of analyzing comprises: calculating variances of the optimizing force field parameters;

testing the variance against preset threshold and returning testing results; and testing the parameters against a preset range of the allowed values and returning the test result.

11. A computer-implemented system for developing molecular mechanics force field parameters for computer simulations of molecular systems, comprising:

a) means of creating or importing molecular models that represent said molecular systems to be parameterized;

b) means of searching a database for matches between said molecular models and stored molecular models and retrieving stored parameters if complete matches are found;

c) means of preparing input data for quantum mechanics ab initio calculations for said molecular models;

d) means of importing calculated data of said quantum mechanics ab initio calculations for said molecular models;

e) means of selecting force field type and functional forms, and assigning atom types to said molecular models;

f) means of estimating initial force field parameters for said molecular models based on said database or a set of mathematical formulas for said molecular models;

g) means of optimizing said initial force field parameters to fit said input data of quantum mechanics ab initio calculations;

h) means of validating the optimized force field parameters; and i) means of exporting said optimized force field parameters in required formats to external molecular mechanics simulation packages and saving the molecular models, input data and optimize force field parameters to said database.

12. The system of claim 11, wherein said database is a database of molecular models, their force field parameters and the data for deriving the force field parameters.

13. The system of claim 11, wherein said force field type is a collection of mathematical functions that describe interaction energies and said atom types are symbols representing atoms in different chemical environments.

14. The system of claim 11, wherein said default atom types are symbols used independent of force field types.

15. The system of claim 11, wherein said initial force field parameters are parameters made based on the said database or said mathematical formulas.

* * * * *